US00PP36838P3

(12) United States Plant Patent
Olesen

(10) Patent No.: US PP36,838 P3
(45) Date of Patent: Jul. 22, 2025

(54) FLORIBUNDA ROSE PLANT NAMED 'Poulnap008'

(50) Latin Name: *Rosa hybrida*
Varietal Denomination: Poulnap008

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 18/831,186

(22) Filed: Sep. 5, 2024

(65) Prior Publication Data

US 2025/0107472 P1 Mar. 27, 2025

(30) Foreign Application Priority Data

Sep. 22, 2023 (QZ) ..... PBR 20231974

(51) Int. Cl.
*A01H 5/02* (2018.01)
*A01H 6/74* (2018.01)

(52) U.S. Cl.
USPC ..... Plt./148
CPC ..... *A01H 6/749* (2018.05)

(58) Field of Classification Search
USPC ..... Plt./148, 147, 140, 107, 106, 105
CPC . A01H 5/02; A01H 5/00; A01H 6/749; A01H 6/74
See application file for complete search history.

(56) References Cited

U.S. PATENT DOCUMENTS

PP35,515 P3 * 12/2023 Olesen ..... A01H 6/749 Plt./130

OTHER PUBLICATIONS

CPVO Application Consultation Version 4.21.4 retrieved on Dec. 3, 2024 at https://online.plantvarieties.eu/publicConsultationDetails?registerId=20231974&denomination=poulnap008, 2 pp. (Year: 2024).*

* cited by examiner

*Primary Examiner* — June Hwu

(57) ABSTRACT

A new garden rose plant of the floribunda class which has abundant, pink and apricot blend flowers with strong fragrance and attractive foliage. This new and distinct variety has shown to be uniform and stable in the resulting generations from asexual propagation.

2 Drawing Sheets

Botanical designation: *Rosa hybrida.*
Variety denomination: 'Poulnap008'.

This application claims priority to Plant Breeder's Rights Application Number 2023/1974, which was filed at the Community Plant Variety Rights Office in the European Union on Sep. 22, 2023, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2013 and the resulting seeds were planted in a controlled environment in Fredensborg, Denmark. The new variety, named 'Poulnap008', originated as a single seedling from the stated cross.

The new variety may be distinguished from its male pollen parent and female seed parent primarily by the following characteristics. The male pollen parent plant has larger flowers in less abundance than the claimed plant. The female seed parent plant has red flowers while the new variety has flowers with a pink and apricot color blend.

The objective of the hybridization of this rose variety was to create a new and distinct garden rose variety with unique qualities, such as:

1. Uniform and abundant pink and apricot blend flowers with perfume;
2. Vigorous, but compact growth when propagated on its own roots;
3. Exceptional disease resistance.

This combination of qualities is not present in previously available commercial cultivars of this type, known to the inventor, and distinguish 'Poulnap008' from all other varieties of which we are aware.

As part of the rose development program, Mogens N. Olesen germinated the seeds from the aforementioned hybridization during winter of 2013 and conducted evaluations on the resulting seedlings in a controlled environment in Fredensborg, Denmark. 'Poulnap008' was selected in the spring of 2014 by the inventor as a single plant from the progeny of the aforementioned hybridization.

Asexual reproduction of 'Poulnap008' by rooted cuttings was first done by Mogens N. Olesen in the nursery in Fredensborg, Denmark in July 2014. This initial and other subsequent asexual propagations conducted in controlled environments have demonstrated that the characteristics of 'Poulnap008' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulnap008'.

Specifically illustrated in FIG. 1 of the drawings are open flowers at various stages of development viewed from above, a flower bud and one quarter opened flower viewed from the side, a fully open flower viewed from the side, and flower petals detached revealing reproductive flower parts.

Figure 1:
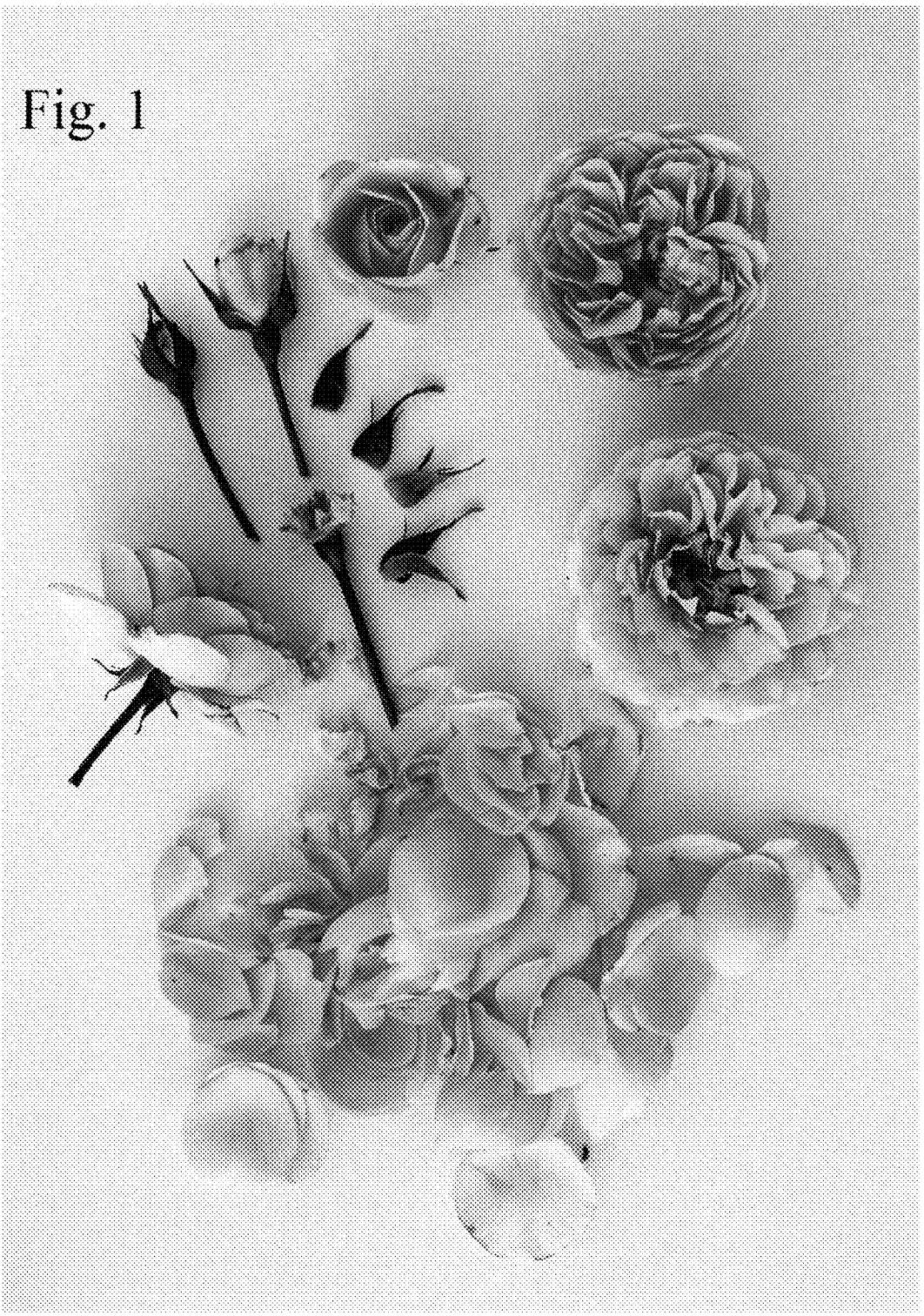
Figure 2:
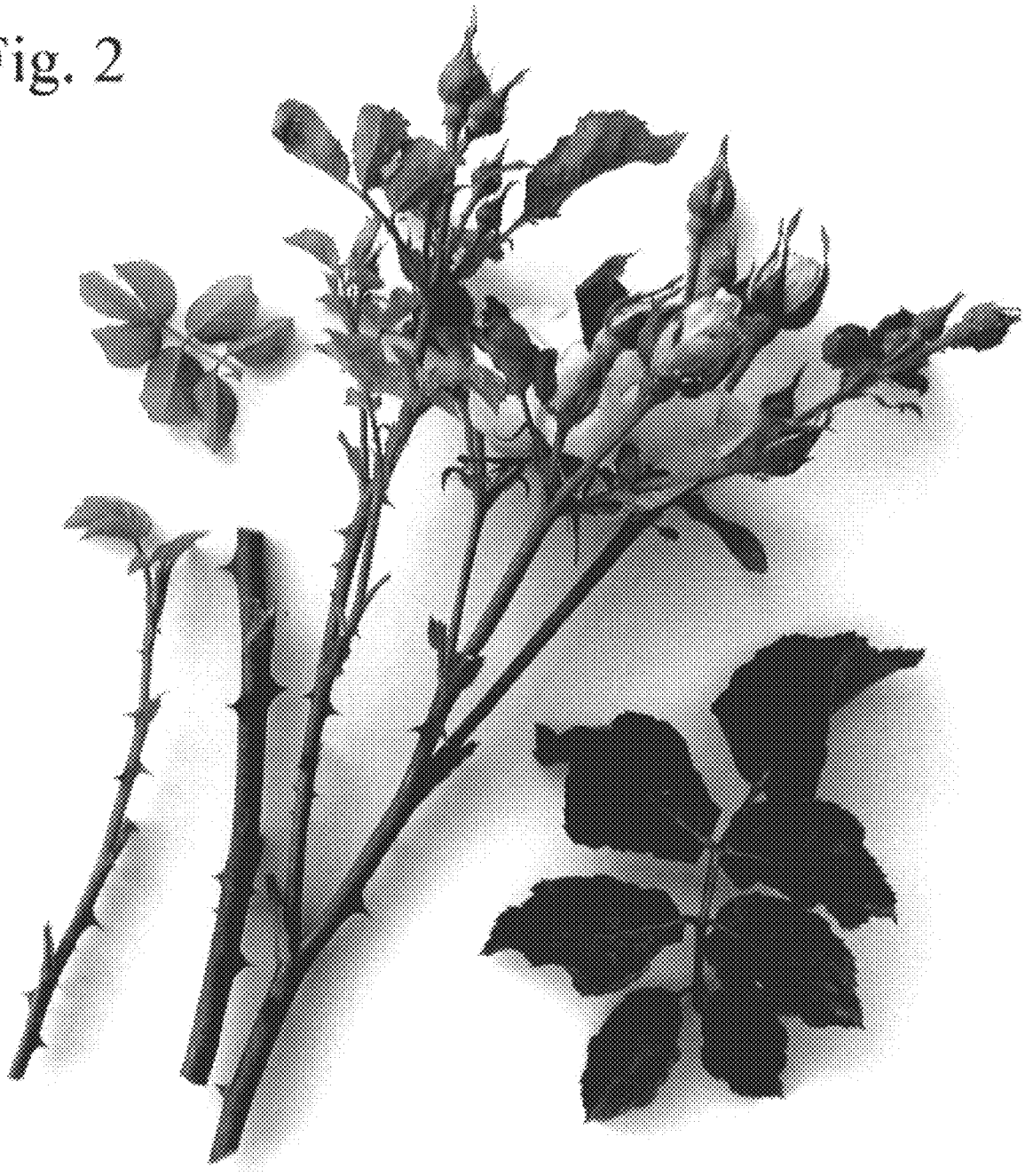

Specifically illustrated in FIG. 2 of the drawings is a cluster of flower buds on the branch, juvenile growth, a bare stem exhibiting prickles, and a mature compound leaf. Plants shown are 15 months old.

DETAILED DESCRIPTION OF THE VARIETY

The following is a description of 'Poulnap008', as observed in its growth in an outdoor nursery in Odense Denmark. Observed plants are 15 months of age, and were grown on their own roots in 30 cm pots. Color references are made using The Royal Horticultural Society (London, England) Colour Chart, 2001, except where common terms of color are used.

For a comparison, several physical characteristics of the rose variety 'Poulren036', U.S. Plant Pat. No. 35,515 are compared to the claimed plant. While 'Poulnap008' has, in quantity, about 83 petals, 'Poulren036' has about 107 flower petals. The color of flower petal inner surface upon opening for that of 'Poulnap008' is described as Yellow Group 12C at the basal zone, middle and marginal zones are Red Group 38B with light shades of Yellow-Orange Group 19C throughout. The inner surface of flower petals upon opening for the comparison variety is Orange-Red Group 32C with a basal zone color Yellow-Orange Group 14B, with a basal zone of Yellow 11 A.

FLOWER AND FLOWER BUD

Blooming habit: Continuous.

Flower bud:

- *Size*.—Upon opening, 30 mm in length from base of receptacle to end of bud. Bud diameter is 13 mm.
- *Bud form*.—Ucerolate.
- *Bud color*.'As sepals divide petals are Yellow Green 8C.
- *Sepal inner surface*.—Color: Yellow-Green Group 145B with intonations of Greyed-Purple Group 183C. Surface: Lightly pubescent.
- *Sepal outer surface*.—Color: Yellow-Green Group 144A with intonations of Greyed-Red Group 183C at the apex. Texture: Smooth.
- *Sepal shape*.—Apex: Cirrhose. Base: Flat at union with receptacle.
- *Sepal margin*.—Margins have weak foliaceous appendages on three of the five sepals.
- *Sepal size*.—About 35 mm long, 11 mm wide.
- *Receptacle*.—Texture: Smooth. Size: 5 mm in height, 7 mm wide. Color: Yellow-Green Group 144A. Shape: Campanulate.
- *Pedicel*.—Surface: Smooth Length: 47 mm. Diameter: 3.5 mm on average. Color: Yellow-Green Group 144A with light intonations of Greyed-Red Group 180A. Strength: Strong.
- *Peduncle*.—Length: 5 to 12 cm. Diameter: About 3 to 4 mm. Color: Yellow-Green Group 144A with intonations of Greyed-Purple Group 183C. Texture: Smooth and with large prickles the color of Greyed-Purple Group 183B.

Flower bud development: Flower buds are borne in clusters of 3 to 5 flower buds on each peduncle. Normally stems have about 5 peduncles.

Flower bloom:

- *Fragrance*.—Strong citrus like perfume.
- *Duration*.—The blooms have a duration on the plant of approximately 18 days. Petals fall clearly away from plant after flowers have fully matured.
- *Size*.—Flower diameter is 75 to 85 mm when open. Flower depth is 35 mm.
- *Flower shape*.—Quartered-rosette, very double, with many overlapping petals packed loosely into quarter sections.
- *Shape of flower, side view*.—The upper portion is flat. The lower portion is concave.

Petalage: Under normal conditions, flowers have about 83 petals.

General tonality of flower: Open flowers are primarily Red Group 49A with intonations of Red Group 38A. After 10 days the color faces to Red Group 38D.

Petal color:

- *Upon opening, outer petals*.—Upper surface: At basal zone a medium sized petal spot the color of Yellow Group 12C. Middle and marginal zone Red Group 38B. Light shades of Yellow-Orange Group 19C throughout. Lower surface: At basal zone Yellow Group 10B. the middle zone is Yellow Group 19C. Marginal zone Red Group 49B and C blended.
- *Upon opening, inner petals*.—Upper surface: At basal zone Yellow Group 12C. Middle and marginal zone Red Group 38B. Light shades of Yellow-Orange Group 19C throughout. Lower surface: At basal zone Yellow Group 10B. the middle zone is Yellow Group 19C. Marginal zone Red Group 49B and C blended.
- *After opening, outer petals*.—Upper surface: Red Group 56B with a medium sized basal intonations of Yellow Group 4D. Lower surface: At the basal zone, Yellow Group 4D. At the middle zone Yellow-Orange Group 19D. Marginal intonations are Red Group 56B.
- *After opening, inner petals*.—Upper surface: At basal zone Yellow Group 12C. Middle and marginal zone Red Group 38B. Light shades of Yellow-Orange Group 19C throughout. Lower surface: At basal zone Yellow Group 10B. The middle zone is Yellow-Group 19C. Marginal zone Red Group 49B and C blended.

Petals:

- *Petal reflex*.—Not reflexed.
- *Margin*.—Entire and uniform. Light undulations.
- *Shape*.—Rounded. Apex shape: Rounded. Base shape: Obtuse.
- *Size*.—45 mm (l)×38 mm (w).
- *Texture*.—Smooth.
- *Thickness*.—Thin.

Petaloids:

- *Size*.—25 mm (l) by 11 mm (w).
- *Quantity*.—About 12.
- *Shape*.—Elliptical with an acute base and rounded apices.

*Color*.—Red Group 38C underneath. The upper side is Red Group 49C. Basal zone and streaking Yellow Group 8B.

Reproductive flower parts:

*Pollen*.—None observed.

*Anthers*.—Size: 3 mm in length. Color: Yellow Group 11C. Quantity: 90 on average.

*Filaments*.—Color: Yellow Group 12A. Length: 5 mm.

*Pistils*.—Length: 10 mm. Quantity: 35 on average.

*Stigmas*.—Color: Yellow Group 160C.

*Styles*.—Color: Red-Purple Group 63B.

*Location of stigmas*.—Superior in location relative to the length of the filaments and the height of the anthers.

*Hips*.—None Observed.

PLANT

Plant growth: Upright, bushy. Plants are 50 cm in height, and 65 cm wide.

Stems:

*Color of juvenile growth*.—Yellow-Green Group 145A with strong intonations of Greyed-Red Group 178B.

*Color of mature growth*.—Yellow-Green Group 146B.

*Length*.—Canes are about 23 cm from the base of the plant to the flowering portion.

*Diameter*.—About 4 mm.

*Internodes*.—On mature canes about 45 mm between nodes.

*Surface texture*.—Young wood: Smooth. Older wood: Somewhat rough.

Long prickles:

*Incidence*.—About 13 prickles per 10 cm of stem.

*Size*.—Average length of prickles on mature stems is 7 mm.

*Shape*.—Upper portion is concave. Lower portion is concave.

*Color*.—Juvenile prickles: Greyed-Purple Group 184D and Yellow-Green Group 144C. Mature prickles: Greyed-Purple Group 183C.

Plant foliage:

*Compound leaf*.—12.5 cm long×10.5 cm wide.

*Quantity*.—2 leaves per 10 cm of stem on average.

*Leaf bearing angle to the stem*.—45 degrees.

*Color of juvenile foliage*.—Upper side: Yellow-Green Group 144A shaded with Greyed-Red Group 180A. Lower side: Yellow-Green Group 144B.

*Color of mature foliage*.—Upper side: Yellow-Green Group 147A. Lower side: Yellow-Green Group 147B.

Plant leaves and leaflets:

*Stipules*.—Size: 20 mm long, 3 mm wide. Quantity: 2 per compound leaf. Shape: Linear, slightly broad based with outward extending apices. Margins: Finely serrated. Color: Yellow-Green Group 146A.

*Petiole*.—Length: 44 mm average. Diameter: 3 mm. Upper surface color: Yellow-Green Group 144A. Lower surface color: Yellow-Green Group 144A. Texture: Upper surface is glandular. Lower surface is smooth.

*Rachis*.—Length: 60 mm average. Upper surface color: Yellow-Green Group 144A. Lower surface color: Yellow-Green Group 144A. Texture: Upper surface is glandular. Lower surface is smooth with a few small prickles.

*Leaflet*.—Quantity: Normally 7 leaflets. Margins: Serrated. Moderate undulations. Size: Terminal leaflets are about 55 mm long, 48 mm wide. Shape: Generally elliptical. Base: Cordate or rounded. Apex: Mucronate. Texture: The upper and lower surfaces are smooth. Thickness: Average. Arrangement: Odd pinnate. Venation: Reticulate. Glossiness: The upper surface is glossy. The lower surface is not glossy.

Disease resistance: Above average resistance to powdery mildew *Sphaerotheca pannosa* var. *rosae*, downy mildew *Peronospora sparsa*, rust *Phragmidium* spp., block spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulnap008' substantially as described and illustrated herein.

* * * * *